(12) United States Patent
Kanno et al.

(10) Patent No.: US 8,999,236 B2
(45) Date of Patent: Apr. 7, 2015

(54) DISINFECTION METHOD AND DISINFECTION DEVICE

(75) Inventors: Taro Kanno, Sendai (JP); Keisuke Nakamura, Sendai (JP); Hiroyo Ikai, Sendai (JP); Masahiro Kono, Sendai (JP); Yoshimi Niwano, Sendai (JP)

(73) Assignee: AZ Co., Ltd., Sendai-Shi (JP)

( * ) Notice: Subject to any disclaimer, the term of this patent is extended or adjusted under 35 U.S.C. 154(b) by 0 days.

(21) Appl. No.: 13/807,224

(22) PCT Filed: Dec. 1, 2011

(86) PCT No.: PCT/JP2011/077865
§ 371 (c)(1),
(2), (4) Date: Dec. 27, 2012

(87) PCT Pub. No.: WO2012/098772
PCT Pub. Date: Jul. 26, 2012

(65) Prior Publication Data
US 2013/0108505 A1    May 2, 2013

(30) Foreign Application Priority Data
Jan. 22, 2011 (JP) .................................. 2011-011477

(51) Int. Cl.
*A61L 2/08* (2006.01)
*A61L 2/18* (2006.01)
(Continued)

(52) U.S. Cl.
CPC . *A61L 2/186* (2013.01); *A61L 2/08* (2013.01); *A61L 2/084* (2013.01); *A61L 2/085* (2013.01); *A61L 2/10* (2013.01); *A01N 43/16* (2013.01); *A01N 43/90* (2013.01); *A01N 59/00* (2013.01)

(58) Field of Classification Search
CPC .................................... A61L 2/08; A61L 2/10
USPC ......................................... 422/22, 186.3, 129
See application file for complete search history.

(56) References Cited

U.S. PATENT DOCUMENTS

| 6,908,591 B2 * | 6/2005 | MacPhee et al. ............... 422/22 |
| 2008/0008812 A1 | 1/2008 | Ochiai et al. |
| 2009/0099646 A1 | 4/2009 | Matsuda et al. |

FOREIGN PATENT DOCUMENTS

| CN | 101 028 528 A | 9/2007 |
| EP | 1 426 064 A1 | 6/2004 |

(Continued)

OTHER PUBLICATIONS

Jan. 31, 2012 International Search Report issued in International Patent Application No. PCT/JP2011/077865 (with translation).
(Continued)

*Primary Examiner* — Sean E Conley
(74) *Attorney, Agent, or Firm* — Oliff PLC

(57) ABSTRACT

A disinfection method, a disinfection device, and a disinfecting agent which utilizes light, which can achieve a high disinfection effect within a short time are provided. A disinfecting agent containing catechins is brought into contact with an item to be disinfected, and then the disinfecting agent is irradiated with light. The disinfecting agent preferably comprises an aqueous proanthocyanidin solution produced by polymerizing multiple catechin molecules each having a gallate group. Particularly, the aqueous proanthocyanidin solution preferably has a proanthocyanidin concentration of 0.25 to 4 mg/mL. Light with which the disinfecting agent is irradiated preferably has a wavelength of 350 to 500 nm.

7 Claims, 4 Drawing Sheets

(51) Int. Cl.
*A01N 43/16* (2006.01)
*A01N 43/90* (2006.01)
*A01N 59/00* (2006.01)
*A61L 2/10* (2006.01)

(56) References Cited

FOREIGN PATENT DOCUMENTS

| | | |
|---|---|---|
| JP | A-2008-125515 | 6/2008 |
| JP | A-2008-173049 | 7/2008 |
| JP | A-2008-214297 | 9/2008 |
| JP | A-2009-017839 | 1/2009 |
| JP | A-2011-182790 | 9/2011 |
| WO | WO 2006/083318 A2 | 8/2006 |
| WO | WO 2010/078660 A1 | 7/2010 |
| WO | WO 2011/040424 A1 | 4/2011 |

OTHER PUBLICATIONS

Arakawa et al., "Role of Hydrogen Peroxide in Bactericidal Action of Catechin," *Biol. Pharm. Bull.*, pp. 277-281, vol. 27, No. 3 (2004).
Ikigai et al., "Bactericidal Catechins Damage the Lipid Bilayer," *Biochimica et Biophysica Acta*, pp. 132-136, vol. 1147 (1993).
Kajiya et al., "Interaction of Tea Catechin Derivatives with Lipid Bilayers and Their Antibacterial Activity," FFI Journal, pp. 834-838, vol. 209, No. 10 (2004).
Dec. 6, 2013 European Search Report issued in European Application No. 11856576.1.
Nakamura et al., "Photo-Irradiation of Proanthocyanidin as a New Disinfection Technique via Reactive Oxygen Species Formation," *PLOS One*, Mar. 2013, vol. 8, No. 3, pp. 1-9.

\* cited by examiner $$\text{Catechin-(OH)}_n \rightarrow \text{Catechin-(OH)}_{n-2}(O\cdot)_2 + 2e^- + 2H^+$$

$$2e^- + O_2 + 2H^+ \rightarrow H_2O_2 \rightarrow \text{Anti-bacterial Activity}$$

Light $$2e^- + O_2 + 2H^+ \rightarrow H_2O_2 \rightarrow 2\cdot OH$$

● DMPO-OH
△ DMPO-OOH

Magnet field (mT)

DISINFECTION METHOD AND DISINFECTION DEVICE

TECHNICAL FIELD

The present invention relates to a disinfection method and a disinfection device.

BACKGROUND ART

It has been well known that catechins have disinfection action. This action is ascribed to the ability of the catechins to generate hydrogen peroxide by reducing the dissolved oxygen, which in turn exerts disinfection action (see, for example, Non-Patent Literature 1). In addition, among various catechins, those possessing gallate groups such as epigallocatechin, epicatechin gallate, and epigallocatechin gallate, have higher affinity to cell membrane and thus are known to have stronger disinfection action (see, for example, Non-Patent literature 2 or 3).

CITATION LIST

Non-Patent Literature

Non-Patent Literature 1: H. Arakawa, M. Maeda, S. Okubo and T. Shimamura, "Role of Hydrogen Peroxide in Bactericidal Action of Catechin", Biol. Pharm. Bull., 2004, 27, 3, p. 277-281

Non-Patent Literature 2: H. Ikigai, T. Nakae, Y. Hara, T. Shimamura, "Bactericidal catechins damage the lipid bilayer", Biochimica et Biophysica Acta, 1993, 1147, p. 132-136

Non-Patent Literature 3: K. Kajiya, S. Kumazawa, and T. Nakayama, "Membrane action and anti-bacterial activity of catechin derivatives from tea", Foods & Food Ingredients Journal of Japan, 2004, 209, p. 834-838

SUMMARY OF INVENTION

Technical Problem

As disclosed in Non-Patent literatures 1 to 3, catechins exhibit disinfection action and exert its disinfection effect even at a low concentration. However, in order to achieve sufficient disinfection effect, an extended reaction time of 12 hours or more was required.

The present invention is devised by focusing on this problem, and aims at providing a disinfection method and a disinfection device, that can achieve a high disinfection effect within a short period of time.

Solution to Problem

In order to achieve the above stated object, the disinfection method according to the present invention comprises the steps of: bringing a disinfecting agent containing catechins into contact with an item to be disinfected, and irradiating the disinfection agent with light.

The disinfection method according to the present invention achieves its disinfection effect by the mechanism described below. As shown in FIG. 1, catechins exert disinfection action by reducing the dissolved oxygen ($O_2$) and generating hydrogen peroxide ($H_2O_2$). When the hydrogen peroxide is irradiated with light, hydroxyl radicals ($\cdot OH$) are generated through the photolysis of the hydrogen peroxide, as shown in FIG. 2. Since catechins possess a high antioxidative effect, it may be usually considered that its phenolic hydroxyl group acts as a donor of $e^-$ and $H^+$, while also functioning to extinguish hydroxyl radicals, so as not to produce the disinfection effect.

However, as shown in FIG. 2, the phenolic hydroxyl group, after acting as the donor, eventually assumes quinone structure, and cannot extinguish the hydroxyl radicals. For this reason, in the presence of abundant dissolved oxygen, phenolic hydroxyl group acts as a donor and does not extinguish hydroxyl radicals, thereby achieving the disinfection effect mediated by hydroxyl radicals.

The inventors of the present invention, as discussed above, discovered an unexpected disinfection effect using a method that usually is not associated with having any disinfection effect, thus arriving at the present invention.

According to the disinfection method of the present invention, hydroxyl radicals can be generated by irradiating the disinfecting agent with light after bringing the disinfecting agent containing catechins in contact with the item to be disinfected. Disinfecting effect by hydroxyl radicals can thus be obtained so that the item to be disinfected is disinfected. Hydroxyl radicals thus generated achieves higher disinfecting effect in a shorter period of time compared to the disinfecting effect of catechins observed without light irradiation.

Catechins are more stable and less toxic compared to hydrogen peroxide, therefore, compared to the disinfecting method directly utilizing hydrogen peroxide, one can obtain more stable as well as safer disinfecting effect. In the disinfection method according to the present invention, any method can be used in terms of ways of bringing the disinfecting agent in contact with the item to be disinfected, including the method in which the disinfecting agent is applied or sprayed and the method in which the item to be disinfected is submerged in a solution containing the disinfecting agent.

In the disinfection method according to the present invention, catechins such as catechin, epicatechin, epigallocatechin, epicatechin gallate, epigallocatechin gallate, gallocatechin, catechin gallate, and gallocatechin gallate may be used alone, or in combinations of more than two kinds, or in a form in which one or two kinds or more are polymerized in multitude (for example, proanthocyanidin). However, catechins that have gallate groups are especially preferable. Catechins having gallate groups exhibit higher affinity to cell membrane and exert higher disinfecting effect on the subject of disinfection that has cell membrane. Furthermore, in comparison with the catechins not having gallate groups, catechins having gallate groups generate more hydrogen peroxide by reducing the dissolved oxygen, so that the amount of hydroxyl radicals generated by light irradiation also increases, thereby further improving the disinfecting effect.

In the disinfection method according to the present invention, the disinfecting agent may comprise only catechins or may also contain other substances. Other substances may be any substances including water, disinfecting agent, saccharide, coloring agent, fragrance agent, seasoning, synthetic or natural disinfecting agent. The disinfecting agent other than catechins includes strongly acidic water, iodine preparation (such as iodine tincture, povidone-iodine and the like), chlorides (such as sodium hypochlorite and the like), mercurochrome solution, chlorhexidine gluconate, acrinol, alcohols (such as ethyl alcohol) and hydrogen peroxide solution. However, substances that are safe are more preferable.

The disinfecting agent containing catechins preferably comprises a solution containing the catechins, and more preferably comprises aqueous proanthocyanidin solution. Furthermore, the aqueous proanthocyanidin solution preferably has a proanthocyanidin concentration of 0.25 to 4 mg/mL. Proanthocyanidin is a substance in which multiple catechins are polymerized. As such, it can provide high disinfecting effect with superior safety.

In the disinfection method according to the present invention, the light can be of any wavelength such as ultraviolet light or infrared light, as long as it can generate hydroxyl radicals from hydrogen peroxide, however, the wavelength of 350 nm to 500 nm is more preferable. In this case also, high disinfecting effect as well as high safety can be achieved. Especially, safety can further be improved if visible light is used.

The irradiance of the irradiation light is preferably no less than 300 mW/cm$^2$ or more, and larger the irradiance, more effective is the light.

The disinfection device according to the present invention is characterized by comprising a disinfecting agent comprising an aqueous proanthocyanidin solution having the proanthocyanidin concentration of 0.25 to 4 mg/mL, and light emitting means provided to be capable of irradiating the disinfecting agent that is in contact with an item to be disinfected with light having a wavelength of 350 to 500 nm.

The disinfection device according to the present invention can suitably execute the disinfection method according to the present invention. According to the disinfection device of the present invention, hydroxyl radicals can be generated by bringing the disinfecting agent in contact with the item to be disinfected, followed by irradiating the disinfecting agent with the light using light emitting means for emitting the light. Accordingly, this achieves the high disinfecting effect due to proanthocyanidin and leads to the disinfection of the object to be disinfected. Furthermore, proanthocyanidin has low toxicity and therefore is very safe.

In the disinfection method and disinfection device according to the present invention, the light emitting means can be of any type, for example, incandescent lamp, fluorescent lamp, halogen lamp, xenon lamp, LED (light emitting diode), semiconductor laser, or those utilizing sun light. The irradiated light can be single wavelength light, light containing multiple wavelengths, or light containing a prescribed band of wavelengths.

The disinfecting agent that utilizes light concerning the present invention is characterized by containing an aqueous proanthocyanidin solution, and further characterized by having the proanthocyanidin concentration of 0.25 to 4 mg/mL.

The disinfecting agent that utilizes light concerning the present invention is suitably used as the disinfecting agent in the disinfection method and the disinfection device concerning the present invention. The disinfecting agent of the present invention is used by applying or spraying on the item to be disinfected. Subsequent irradiation of light generates hydroxyl radicals, and the item to be disinfected is disinfected by the action of the hydroxyl radicals. Furthermore, proanthocyanidin has low toxicity, therefore, is highly safe.

The disinfection method and the disinfection device according to the present invention, as well as the disinfecting agent that utilizes light concerning the present invention, are preferably, suitably selected depending on the item to be disinfected. For example, if the item to be disinfected is comprised of tooth or dentures in oral cavity, the disinfecting agent preferably constitutes tooth paste, mouth wash, or rinsing agent for dental treatment and the like.

Advantageous Effects of Invention

According to the present invention, a disinfection method and a disinfection device that can achieve a high disinfection effect in a short period of time, are able to be provided.

DESCRIPTION OF EMBODIMENTS

Hereinafter, description will be given for the disinfection method and the disinfection device of the present invention.

The disinfection method and the disinfecting agent of the disinfection device of the present invention comprise an aqueous proanthocyanidin solution, light emitting means for irradiating the disinfecting agent with light comprises a semiconductor laser capable of irradiating with light having the wavelength of 405 nm.

In regard to the disinfection method and the disinfection device, tests were performed to examine their characteristics and effects as Examples.

EXAMPLES

Example 1

First of all, a qualitative and quantitative analysis of the oxygen radical species generated by light irradiation to proanthocyanidin was performed. The qualitative and quantitative analysis of the oxygen radicals was performed by the Electron Spin Resonance (ESR) spin trapping method. As the spin trapping agent, 5,5-dimethyl-1-pyrrolidone N-oxide (DMPO; from Labotec Co., Ltd.) was used.

In order to examine the effect of a proanthocyanidin concentration with respect to the amount of oxygen radicals generated, 150 µL of aqueous proanthocyanidin solution (from Indina Japan Co., Ltd.) and 150 µL of DMPO were mixed in a microplate (96 wells) such that the final concentration of proanthocyanidin became 0 to 4 mg/mL and that of DMPO became 300 mM. The samples in the wells were irradiated with a 405 nm laser light at the output of 300 mW (irradiance of 940 mW/cm$^2$) for 60 seconds and ESR measurements were made using an ESR device (product name: JES-FA-100, from JEOL Ltd.).

Figure 1:
FIG. 1 is a reaction formula explaining the principle of anti-bacterial activity of catechins.
Figure 1:
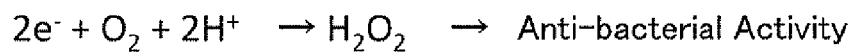
Figure 2:
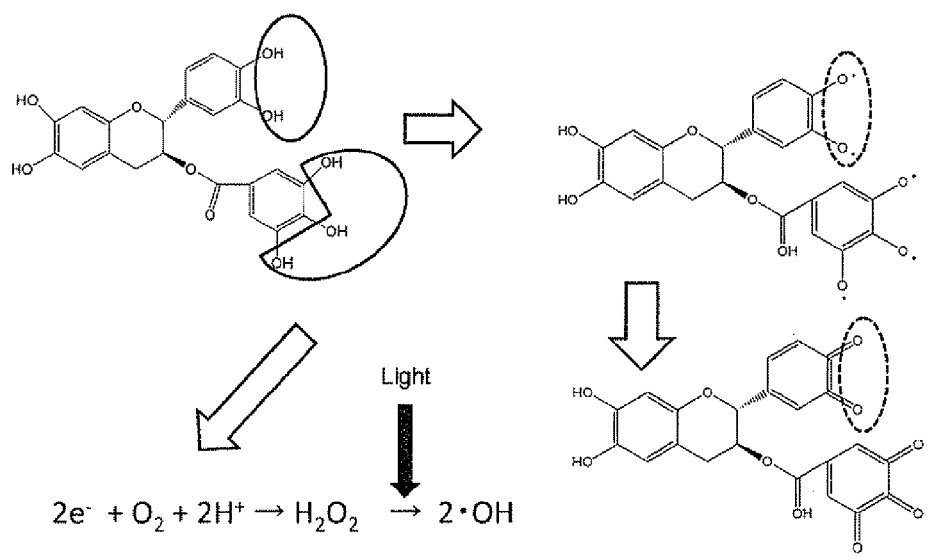
FIG. 2 is a structural formula and a reaction formula depicting the principle of hydroxyl radical generation in catechins and the change in the phenolic hydroxide group.
Figure 3:
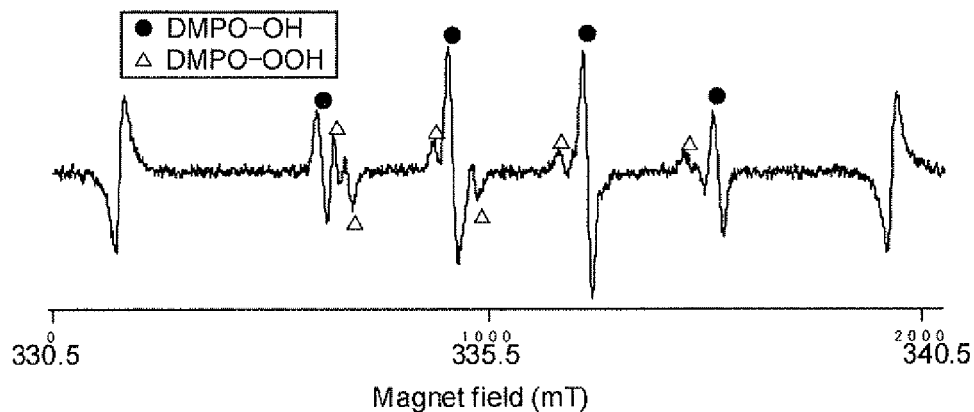
FIG. 3 is an ESR spectrum when a mixed sample containing proanthocyanidin and DMPO is irradiated with light in the disinfection method and the disinfection device according to the embodiment of the present invention.
Figure 4:
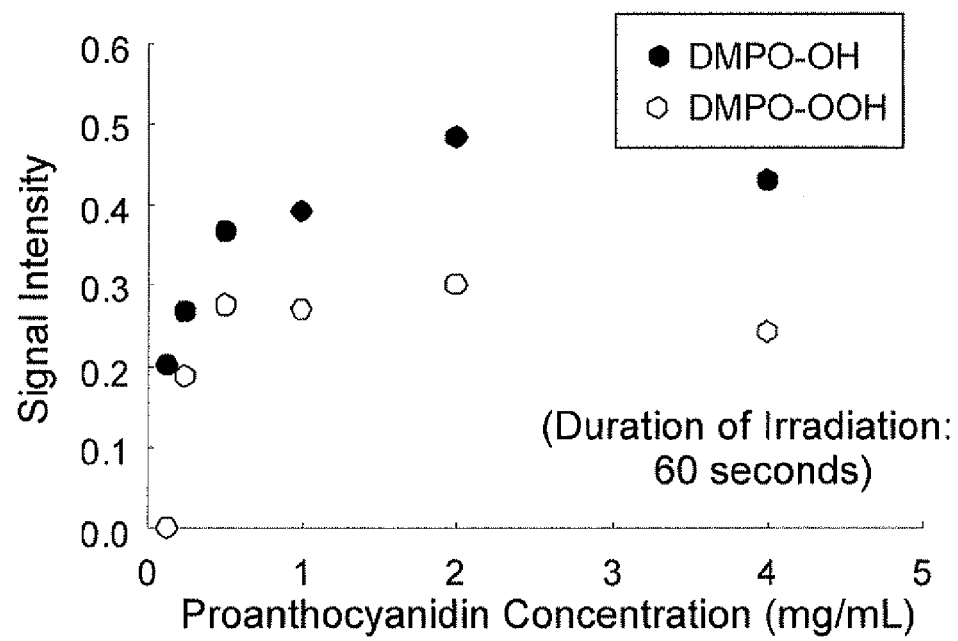
FIG. 4 is a graph showing the effect of proanthocyanidin concentration with respect to the amount of oxygen radical generated in the disinfection method and the disinfection device according to the embodiment of the present invention.
Figure 5:
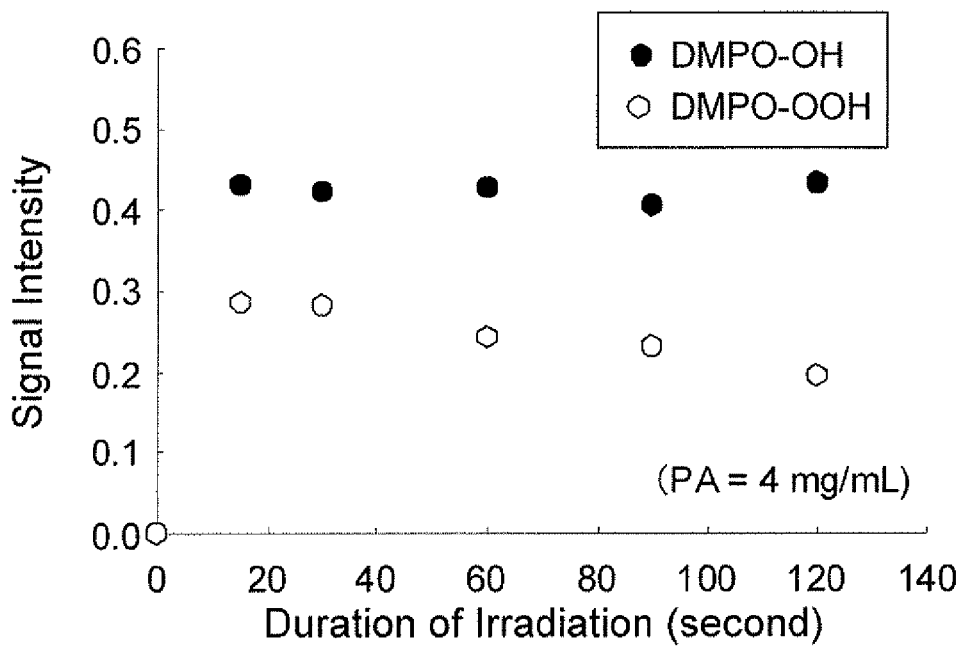
FIG. 5 is a graph showing the effect of the duration of laser irradiation with respect to the amount of oxygen radical generated in the disinfection method and the disinfection device according to the embodiment of the present invention.

The conditions for the ESR measurements were as follows.
field sweep: 330.50-340.50 mT
field modulation frequency: 100 kHz
field modulation width: 0.05 mT
amplitude: 80
sweep time: 2 min
time constant: 0.03 s
microwave frequency: 9.420 GHz
microwave power: 4 mW Obtained ESR spectrum is shown in FIG. 3. Amounts of respective oxygen radicals generated were obtained as relative intensity to a signal obtained from a manganese marker that is installed in the ESR device. Results are shown in FIG. 4. In addition, in order to examine the effect of the duration of laser irradiation with respect to the amount of oxygen radicals generated, further ESR analysis was performed with a fixed concentration of proanthocyanidin (PA) of 4 mg/mL, and durations of laser irradiation ranging from 0 to 120 seconds, while other conditions were kept unchanged. The results are shown in FIG. 5.

As shown in FIG. 3, a hyperfine structure constant of obtained ESR spectrum was analyzed and qualitative analysis was performed. As the result, by irradiating proanthocyanidin with light, formation of DMPO-OH (spin trapping of hydroxyl radical) and DMPO-OOH (spin trapping of superoxide) were confirmed.

As shown in FIG. 4, signal intensities of DMPO-OH and DMPO-OOH increased up to the proanthocyanidin concentration of 1 mg/mL, however, the signal intensity became saturated above that concentration. In addition, as shown in FIG. 5, it was confirmed that the duration of laser irradiation has hardly any effect on the formation of DMPO-OH and DMPO-OOH. This is likely due to the fact that the reaction of forming DMPO-OH and DMPO-OOH by the hydroxyl radicals and super oxides generated from proanthocyanidin is in equilibrium with the reaction of extinguishing the hydroxyl radicals and superoxides by the excess proanthocyanidin.

Example 2

Following experiment was performed in order to evaluate the ability of proanthocyanidin to extinguish oxygen radicals. The amount of hydroxyl radicals generated by ultrasonic scission of water, extinguished by the addition of proanthocyanidin was examined. An ultrasonic wave generator having the frequency of 1650 kHz and output of 30 W was used for ultrasonic wave irradiation. 100 µL of aqueous proanthocyanidin solution and 100 µL of DMPO were mixed in a glass test tube such that the final concentration of proanthocyanidin became 0 to 64 mg/mL and that of DMPO became 150 mM. After mixing, the samples were immediately set to an ultrasonic wave generator and irradiated with ultrasonic wave for 30 seconds. Subsequently, ESR measurements were made. The conditions for ESR measurements were identical to those used in Example 1. The results of the measurements are shown in FIG. 6.

In addition, the ability of proanthocyanidin to extinguish superoxide was evaluated. Superoxide was generated by the hypoxanthine/xanthine oxidase reaction system. 50 µL of hypoxanthine, 30 µL of dimethylsulfoxide, 50 µL of aqueous proanthocyanidin solution, 20 µL of DMPO and 50 µL of xanthine oxidase were mixed in this order, such that the final concentration of hypoxanthine was 500 µM, that of proanthocyanidin was 0 to 1 mg/mL, that of DMPO was 300 mM, and that of xanthine oxidase was 0.1 U/mL. After the addition of xanthine oxidase, the samples were mixed for seconds, and subjected to ESR measurements. The conditions for ESR measurements were identical to those used in Example 1. The results of the measurements are shown in FIG. 7.

Figure 6:
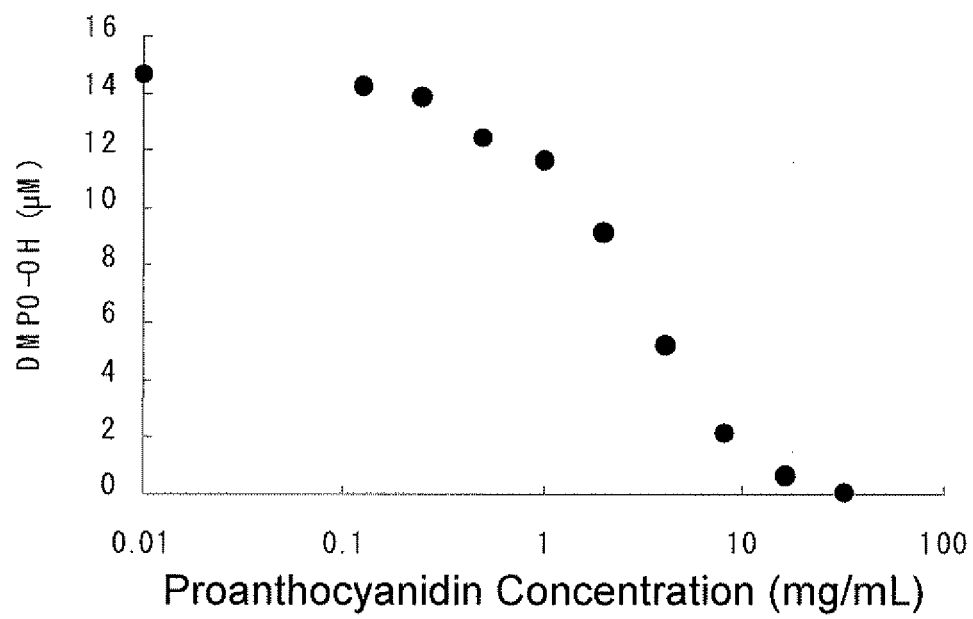
FIG. 6 is a graph showing the hydroxyl radical extinguishing activity of proanthocyanidin in the disinfection method and the disinfection device according to the embodiment of the present invention.

As shown in FIG. 6, 30 seconds of ultrasonic scission of water produced about 15 µM of hydroxyl radicals. Addition of proanthocyanidin to the reaction system suppressed the formation of DMPO-OH in a concentration dependent manner. At the concentration of about 60 mg/mL of proanthocyanidin, it was confirmed that DMPO-OH was not at all formed. The IC 50 (median inhibitory concentration) of proanthocyanidin against DMPO-OH generation was 1.5 mg/mL.

Figure 7:
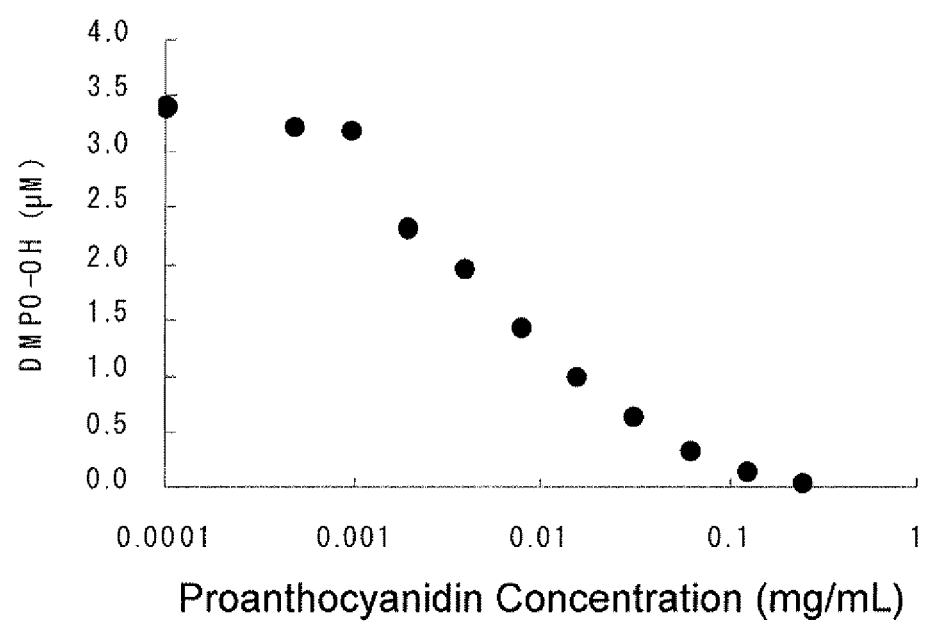
FIG. 7 is a graph showing the superoxide extinguishing activity of proanthocyanidin in the disinfection method and the disinfection device according to the embodiment of the present invention.

In addition, as shown in FIG. 7, DMPO-OOH was generated about 3.5 µM when proanthocyanidin was not added. Addition of proanthocyanidin to the reaction system decreased the formation of DMPO-OOH in a concentration dependent manner. At the concentration of about 0.25 mg/mL of proanthocyanidin, it was confirmed that DMPO-OOH was not formed. The IC 50 of proanthocyanidin against DMPO-OOH generation was 0.005 mg/mL.

Example 3

Disinfection test was carried out to examine the disinfecting effect of the disinfection method and the disinfection device according to the embodiment of the present invention. As the bacteria, Streptococcus aureus ATCC 25923 was used, and subjected to the test as a suspension in physiological saline solution at 2×10$^7$ cells/mL. 150 µl of bacteria suspension and 150 µL of proanthocyanidin was mixed in a microplate and irradiated with 405 nm laser at 300 mW (irradiance of 940 mW/cm$^2$) for 10 minutes.

The effect of concentration with respect to the disinfecting effect was examined by making the final concentrations of proanthocyanidin 4 µg/mL to 3.2 mg/mL. After the irradiation, 50 µL of the sample and 50 µL of 5000 U/mL catalase were mixed to stop the reaction of hydrogen peroxide derived from proanthocyanidin. Subsequently, series of 10 times dilutions were prepared and inoculated on Brain Heart Infusion (BHI) agar medium, cultured at 37° C. for 24 hours under the aerobic condition, and the disinfecting effect was determined. As the controls, the disinfecting effects of proanthocyanidin alone (1 mg/mL) and laser irradiation alone were also evaluated.

Figure 8:
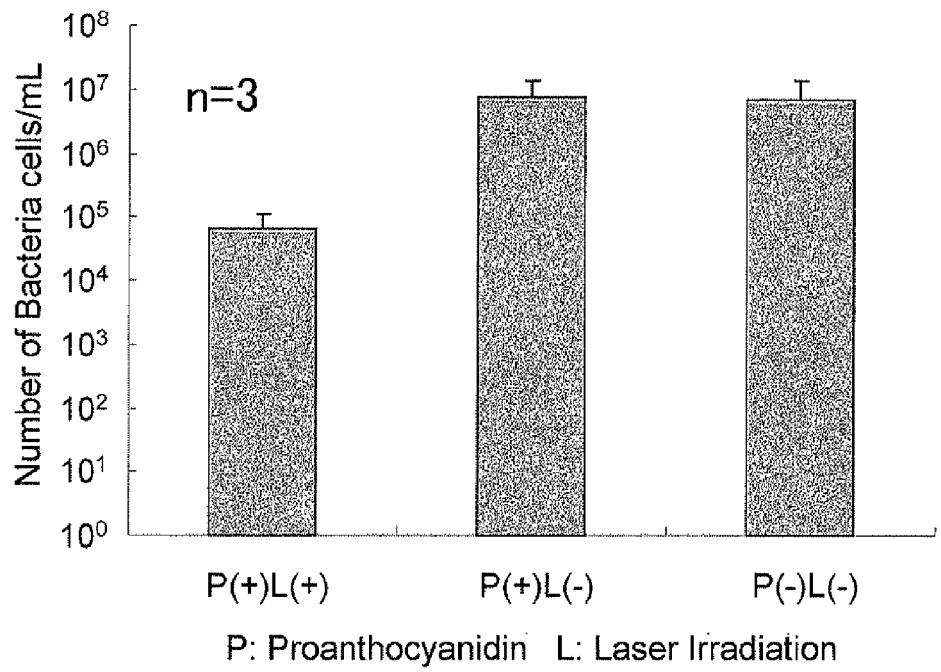
FIG. 8 is a graph showing the disinfecting effect of proanthocyanidin and laser irradiation in the disinfection method and the disinfection device according to the embodiment of the present invention.
Figure 9:
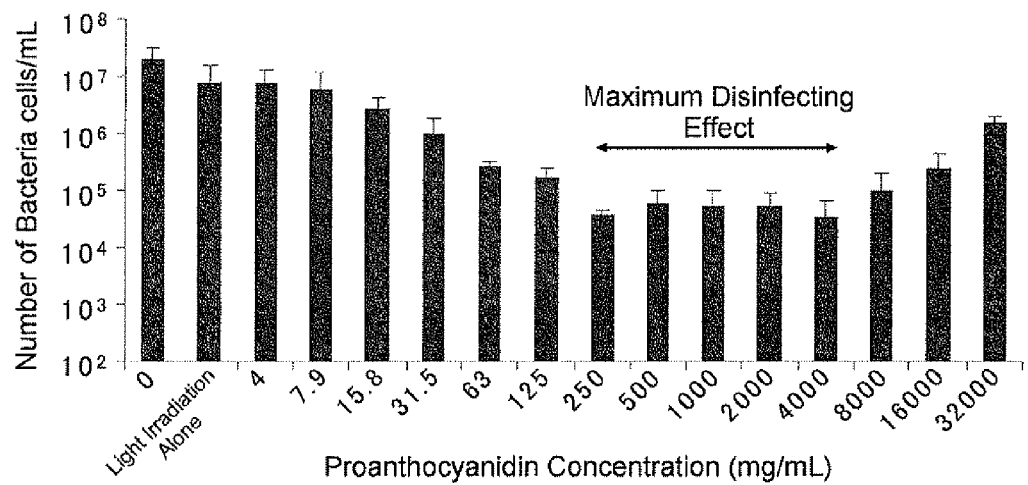
FIG. 9 is a graph showing changes in the disinfecting effect by different concentrations of proanthocyanidin in the disinfection method and the disinfection device according to the embodiment of the present invention.

The test results obtained with proanthocyanidine concentration of 1 mg/mL with or without the laser irradiation, and those with neither proanthocyanidin nor laser irradiation are shown in FIG. 8. In addition, the test results obtained by performing laser irradiation while changing the proanthocyanidin concentrations are shown in FIG. 9.

As shown in FIG. 8, *S. aureus* used in the test was confirmed to be hardly disinfected by proanthocyanidin alone. In addition, as shown in FIG. 9, *S. aureus* was also found to be hardly disinfected by 10 minutes of laser irradiation alone. Whereas, disinfecting effect was observed when a sample in which bacteria and proanthocyanidin were mixed was irradiated with laser. Especially, the highest disinfecting effect of 99% or more was observed when the proanthocyanidin concentration was 0.25 to 4 mg/mL.

It was further confirmed that when the concentration of proanthocyanidin was either lower than 0.25 mg/mL or higher than 4 mg/mL, the disinfecting effect was attenuated. High disinfecting effect was only observed within a limited range of concentrations, most likely, due to the relation between the disinfecting effect of hydroxyl radicals generated by irradiating proanthocyanidin with laser and the antioxidative action of excess proanthocyanidin. In other words, when the concentration of proanthocyanidin is increased, at first, the catechins contained in the increasing amount of proanthocyanidin reduce the dissolved oxygen and produce hydrogen peroxide which is then photolysed by laser irradiation to generate more hydroxyl radicals, thus increasing disinfecting effect. However, when the concentration of proanthocyanidin becomes high and the amount of dissolved oxygen reduced by catechins becomes low, the excess catechins would extinguish hydroxyl radicals already produced, thereby reducing disinfecting effect. In addition, it is also possible that the darker color of highly concentrated aqueous proanthocyanidin solution absorbed laser light and hindered the reaction from hydrogen peroxide to hydroxyl radicals.

Thus, according to the embodiment of the disinfection method and the disinfection device of the present invention, the disinfecting effect by the hydroxyl radicals generated by irradiating the disinfecting agent with light can be achieved and be used to disinfect the item to be disinfected. Furthermore, the synergistic effect of the disinfecting effect derived from catechins and the disinfecting effect derived from hydroxyl radicals can be achieved. By the actions of the generated hydroxyl radicals, higher disinfecting effect can be achieved in shorter period of time, compared to the disinfecting effect of catechins without light irradiation. Proanthocyanidin comprising catechins is stabler and less toxic compared to hydrogen peroxide, therefore, in comparison to the disinfection method directly utilizing hydrogen peroxide, the present invention provides stabler disinfecting effect in significantly safer manner.

The invention claimed is:

1. A disinfection method for disinfecting an item in an oral cavity, comprising the steps of:
    bringing a disinfecting agent containing catechins into contact with the item, and irradiating the contacted item with light having a wavelength of 350 nm to 500 nm.

2. The disinfection method according to claim 1, wherein the catechins have a gallate group.

3. The disinfection method according to claim 1, wherein the disinfecting agent comprises an aqueous proanthocyanidin solution.

4. The disinfection method according to claim 3, wherein the concentration of proanthocyanidin in the aqueous proanthocyanidin solution is 0.25 to 4 mg/mL.

5. The disinfection method according to claim 1, wherein the disinfecting agent further comprises a hydrogen peroxide solution.

6. The disinfection method according to claim 2, wherein the disinfecting agent comprises an aqueous proanthocyanidin solution.

7. The disinfection method according to claim 6, wherein the concentration of proanthocyanidin in the aqueous proanthocyanidin solution is 0.25 to 4 mg/mL.

* * * * *